(12) United States Patent
Ishizeki et al.

(10) Patent No.: US 7,438,700 B2
(45) Date of Patent: Oct. 21, 2008

(54) MEDICINE ADMINISTERING DEVICE FOR NASAL CAVITIES

(75) Inventors: Kazunori Ishizeki, Gunma (JP); Hisatomo Ohki, Gunma (JP); Shigemi Nakamura, Gunma (JP); Akira Yanagawa, Yokohama (JP)

(73) Assignees: Hitachi, Ltd., Tokyo-To (JP); Dott Limited Company, Kanagawa (JP)

( * ) Notice: Subject to any disclaimer, the term of this patent is extended or adjusted under 35 U.S.C. 154(b) by 150 days.

(21) Appl. No.: 10/792,575

(22) Filed: Mar. 4, 2004

(65) Prior Publication Data

US 2004/0176719 A1    Sep. 9, 2004

(30) Foreign Application Priority Data

Mar. 5, 2003    (JP) .............................. 2003-058837

(51) Int. Cl.
*A61M 13/00*    (2006.01)

(52) U.S. Cl. ....................................................... 604/58

(58) Field of Classification Search ................. 604/212, 604/37, 185, 58, 217, 275, 57; 401/185, 401/186; D24/115; 222/95, 215, 213, 282, 222/547, 552, 564, 565, 566, 529, 481, 212, 222/214

See application file for complete search history.

(56) References Cited

U.S. PATENT DOCUMENTS 4,457,453 A * 7/1984 Stevens et al. ................ 222/48

| 4,513,891 A | 4/1985 | Hain et al. |
| 2002/0046751 A1 | 4/2002 | Macrae et al. |
| 2004/0082907 A1 * | 4/2004 | James .......................... 604/58 |

FOREIGN PATENT DOCUMENTS

| GB | 1 103 534 A | 2/1968 |
| JP | 03-066382 A | 3/1991 |
| WO | WO 02/062416 A | 8/2002 |

* cited by examiner

*Primary Examiner*—Kevin C. Simmons
*Assistant Examiner*—Catherine N Witczak
(74) *Attorney, Agent, or Firm*—Sughrue Mion, PLLC

(57) ABSTRACT

A medicine administering device for nasal cavities of a patient suffering from nasal allergy or the like. The medicine administering device comprises a medicine administering device main body including a part defining a powdery medicine accommodating chamber, and a spray nozzle located at a tip end side of the main body. A pump is disposed at a base end side of the medicine administering device main body to discharge air within the pump through the powdery medicine accommodating chamber to the spray nozzle upon being pressed from an outside of the pump. Additionally, a restricting device is disposed within the pump to restrict a displacement amount of the pump in accordance with first and second kinds of pressing positions at which the pump is pressed. The first and second kinds of pressing positions lie respectively in first and second directions which are perpendicular to each other.

7 Claims, 7 Drawing Sheets

MEDICINE ADMINISTERING DEVICE FOR NASAL CAVITIES

BACKGROUND OF THE INVENTION

This invention relates to improvements in a medicine administering device suitable for administering powdery medicine into the nasal cavities of a patient.

In general, to cure patients suffering from nasal allergy or the like, curing methods in which powdery medicine is administered through nasal cavities of the patients have been employed. In these curing methods, exclusive medicine administering devices or sprayers have been used to administer the powdery medicine into the nasal cavities. Here, the medicine administering devices used in these methods includes a medicine administering device main body which is formed with a powdery medicine accommodating chamber for accommodating powdery medicine therein. The tip end side of the medicine administering device main body is formed as a spray nozzle through which the powdery medicine is sprayed. A pump is disposed at the base end side of the medicine administering device and arranged to discharge air stored inside the pump through the powdery medicine accommodating chamber through the (single) spray nozzle upon being pressed from the outside. Such a medicine administering device is disclosed in Japanese Patent Provisional Publication No. 3-66382.

In order to administer the powdery medicine into the nasal cavities by using the above conventional medicine administering device, first the spray nozzle is inserted into one of left and right nasal cavities. Then, in this state, a movable diaphragm body constituting the pump is put between fingers of the patent and pressed in a manner to collapse the movable diaphragm body. By this, air stored inside the pump is discharged toward the powdery medicine accommodating chamber, so that the powdery medicine within the powdery medicine accommodating chamber is sprayed through the spray nozzle into the nasal cavity under the influence of the discharged air. Subsequently, after the powdery medicine has been administered into the one of the nasal cavities, the spray nozzle is pulled out of the one nasal cavity, and then inserted into the other nasal cavity, upon which the pump is pressed to be operated thereby administering the powdery medicine into the nasal cavity. Thereafter, alternate insertion of the spray nozzle is repeated several times to each of the left and right nasal cavities thereby completing a medicine administration operation to the both nasal cavities.

Now, with the above conventional medicine administering device, the single nozzle is repeatedly inserted alternately into the left and right nasal cavities. However, when the first powdery medicine administration is made, a large amount of the powdery medicine exists in the powdery medicine accommodating chamber, so that a relatively large amount of the powdery medicine is sprayed. When the second, third, fourth, . . . powdery medicine administrations are made, the amount of the powdery medicine existing in the powdery medicine accommodating chamber becomes small, and therefore the amounts of the powdery medicine administered into the nasal cavities are stepwise decreased.

As a result, in case that the left and right nasal cavities are alternately supplied with the powdery medicine, it is difficult to administer equally the powdery medicine into both the nasal cavities. In this regard, the patient is required to contrive a suitable medicine administration operation manner or order for the left and right nasal cavities, for example, to administer the powdery medicine twice into the right nasal cavity after administering the powdery medicine once into the left nasal cavity, and then to administer the powdery medicine once more into the left nasal cavity. Additionally, this requires plural medicine administration operations, so that the medicine administration operation becomes troublesome. Furthermore, even in case that the medicine administration operation has been contrived as discussed above, the amount of the sprayed powdery medicine unavoidably changes depending upon the degree of force for pressing the pump. As a result, there arises the problem that the powdery medicine cannot be necessarily administered equally to the left and right nasal cavities.

SUMMARY OF THE INVENTION

It is an object of the present invention to provide an improved medicine administering device which can effectively overcome drawbacks encountered in conventional medicine administering devices of the similar kinds.

Another object of the present invention is to provide an improved medicine administering device by which powdery medicine can be equally administered to the left and right nasal cavities of a patient under simple operations of the patient.

A further object of the present invention is to provide an improved medicine administering device by which a medicine administration operation can be completed by administering powdery medicine once to each of the left and right nasal cavities of a patient.

The other objects and features of this invention will become understood from the following description with reference to the accompanying drawings.

An aspect of the present invention resides in a medicine administering device for nasal cavities. The medicine administering device comprises a medicine administering device main body including a part defining a powdery medicine accommodating chamber, and a spray nozzle located at a tip end side of the main body. A pump is disposed at a base end side of the medicine administering main body to discharge air within the pump through the powdery medicine accommodating chamber to the spray nozzle upon being pressed from an outside of the pump. Additionally, a restricting device is disposed within the pump to restrict a displacement amount of the pump in accordance with first and second kinds of pressing positions at which the pump is pressed. The first and second kinds of pressing positions lie respectively in first and second directions which are perpendicular to each other.

Another object of the present invention resides in a medicine administering device for nasal cavities. The medicine administering device comprises a medicine administering device main body including a part defining a powdery medicine accommodating chamber, and a spray nozzle located at a tip end side of the main body. Additionally, a pump is disposed at a base end side of the medicine administering device main body to discharge air within the pump through the powdery medicine accommodating chamber to the spray nozzle upon being pressed from an outside of the pump. The pump includes a flat cylindrical body having an elongate loop-shaped transverse cross-section to restrict a displacement amount of the pump in accordance with first and second kinds of pressing positions at which the pump is pressed. The first and second kinds of pressing positions lie respectively in first and second directions which are perpendicular to each other.

BRIEF DESCRIPTION OF THE DRAWINGS

In the drawings, like reference numerals designate like parts and elements throughout all figures, in which.

DETAILED DESCRIPTION OF THE INVENTION

Figure 1:
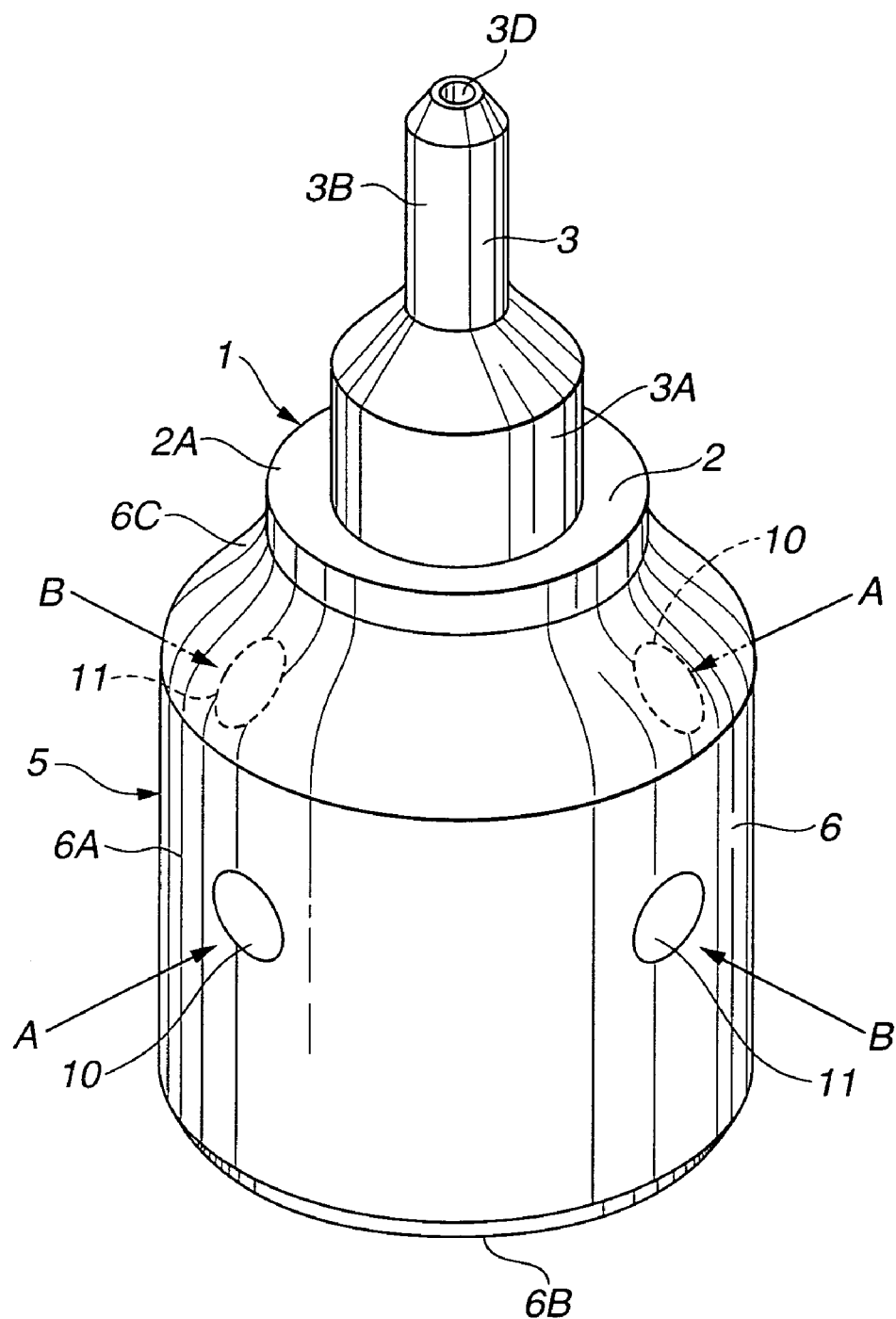
FIG. 1 is a perspective view of a first embodiment of a medicine administering device according to the present invention.

Referring now to FIGS. 1 to 5 of the drawings, an embodiment of a medicine administering device for nasal cavities, according to the present invention is illustrated. The medicine administering device comprises a medicine administering device main body 1 which includes a holder 2 and a spray nozzle 3 which will be discussed in detail after. Holder 2 constitutes a lower side part of medicine administering device main body 1 and includes an annular flange section 2A. A passage-forming section 2B is integral with flange section 2A and located below flange section 2A. A cylindrical section 2C is integral with flange section 2A and located over flange section 2A. Passage-forming section 2B is formed with a valve member accommodating chamber (section) 2D in which a valve member of a one-way discharge valve 8 (discussed after) is movably accommodated.

Passage-forming section 2B is formed with an air supply passage 2E through which valve member accommodating chamber 2D is communicated with a chamber defined inside a generally bottle-shaped movable diaphragm body 6 of a pump 5 which will be discussed in detail after. Passage-forming section 2B is further formed with an air flow passage 2F through which valve member accommodating chamber 2D is communicated with a powdery medicine accommodating chamber 4 which will be discussed in detail after. Air supply passage 2E is communicated through valve member accommodating chamber 2D with air flow passage 2F. In this embodiment, the valve member of discharge valve 8 is arranged to normally close air supply passage 2E and open air supply passage 2E when air flows from air supply passage 2E through valve member accommodating chamber 2D to air flow passage 2F. As shown, cylindrical section 2C is formed at its outer peripheral portion with an external thread 2G.

A spray nozzle 3 is detachably disposed at the upper side of holder 2 and includes a lid section 3A which is located at the base end section of holder 2 and generally cylindrical having an upper end wall (no numeral). A nozzle section 3B is integral with lid section 3A and extends axially upwardly from the upper end wall of lid section 3A. Lid section 3A is formed at its inner peripheral portion with an internal thread 3C which is engageable with the external thread 2G of holder 2. Nozzle section 3B is axially formed with a medicine outflow passage 3D which is communicated with powdery medicine accommodating chamber 4 so that air flow containing powdery medicine from powdery medicine accommodating chamber 4 flows through medicine outflow passage 3D.

Figure 5:
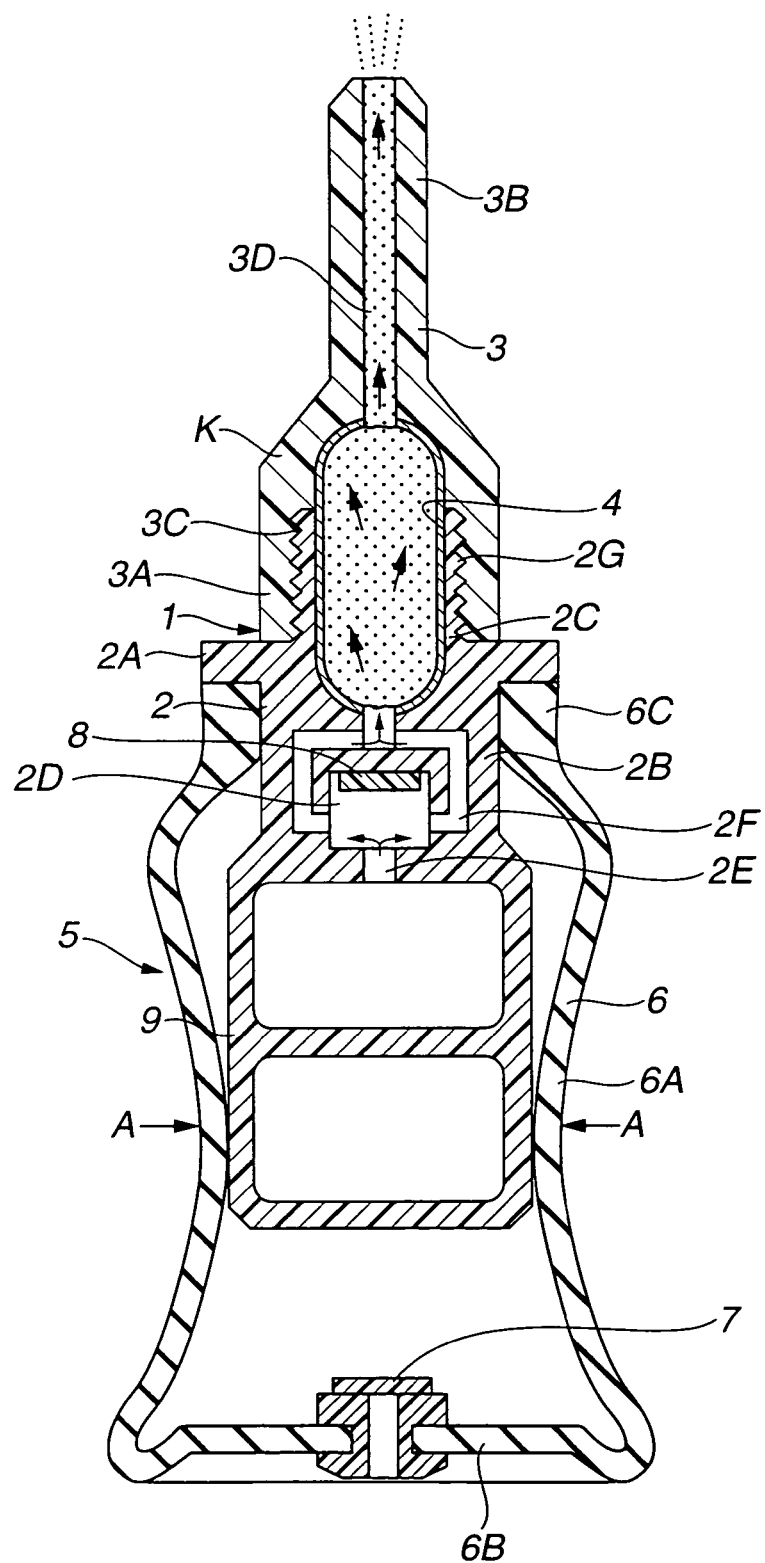
FIG. 5 is a vertical cross-sectional view of the medicine administering device of FIG. 1, showing an initial medicine administration operation at which the movable diaphragm body is pressed in a first pressing direction.

Powdery medicine accommodating chamber 4 is formed between holder 2 and spray nozzle 3. Specifically, a part of powdery medicine accommodating chamber 4 is formed in an upper part of the lid section 3A while the other part of powdery medicine accommodating chamber 4 is formed in holder 2. When spray nozzle 3 is assembled to holder 2, powdery medicine accommodating chamber 4 is formed as a space which extends axially throughout cylindrical section 2C and lid section 3A, in which a major part of powdery medicine accommodating chamber 4 is formed inside the cylindrical section 2C of holder 2. Powdery medicine is, for example, filled in a capsule K and accommodated in powdery medicine accommodating chamber 4 as shown in FIG. 5.

Pump 5 is disposed at the base end side of medicine administering device main body 1 and includes generally bottle-shaped movable diaphragm body 6. Pump 5 is arranged to discharge air held thereinside through powdery medicine accommodating chamber 4 toward spray nozzle 3 by putting the movable diaphragm body 6 between fingers of a person or patient and then by pressing the movable diaphragm body 6 radially inwardly from the outside of movable diaphragm body 6 with the fingers of the patient.

Movable diaphragm body 6 constitutes an outer part of pump 5 and is formed of a rubber (elastomeric) material having an elasticity. More specifically, movable diaphragm body 6 includes a relatively large diameter cylindrical section 6A. A disc-shaped bottom section 6B is integral with cylindrical section 6A and located to close a bottom of cylindrical section 6A. An installation mouth section or open end section 6C is integral with cylindrical section 6A and formed at an open upper-end side of cylindrical section 6A. Installation mouth section 6C of movable diaphragm body 6 is fitted around passage-forming section 2B of holder 2 in such a manner to maintain an air-tight seal between installation mouth section 6C and passage-forming section 2B. Additionally, cylindrical section 6A of movable diaphragm body 6 is provided at its outer surface with pressing marks 10, 11 which will be discussed after.

A one-way suction valve 7 forming part of pump 5 is disposed at bottom section 6B and arranged to open when outside air is sucked into the inside of the movable diaphragm body 6. In this connection, discharge valve 8 forming part of pump 5 is disposed in passage-forming section 2B and arranged to open when air is discharged from the inside of movable diaphragm body 6.

A restriction member or restricting device 9 is disposed inside movable diaphragm body 6 of pump 5 to restrict an inward movement of movable diaphragm body 6. Restriction member 9 is arranged to restrict an inward displacement amount of movable diaphragm body 6 upon putting movable diaphragm body 6 between the fingers and then pressing movable diaphragm body 6 with the fingers, in accordance with two kinds of pressing positions which lie respectively in two directions which are perpendicular to each other. The two kinds of pressing positions correspond respectively to and are indicated respectively by pressing marks 10, 11.

Figure 2:
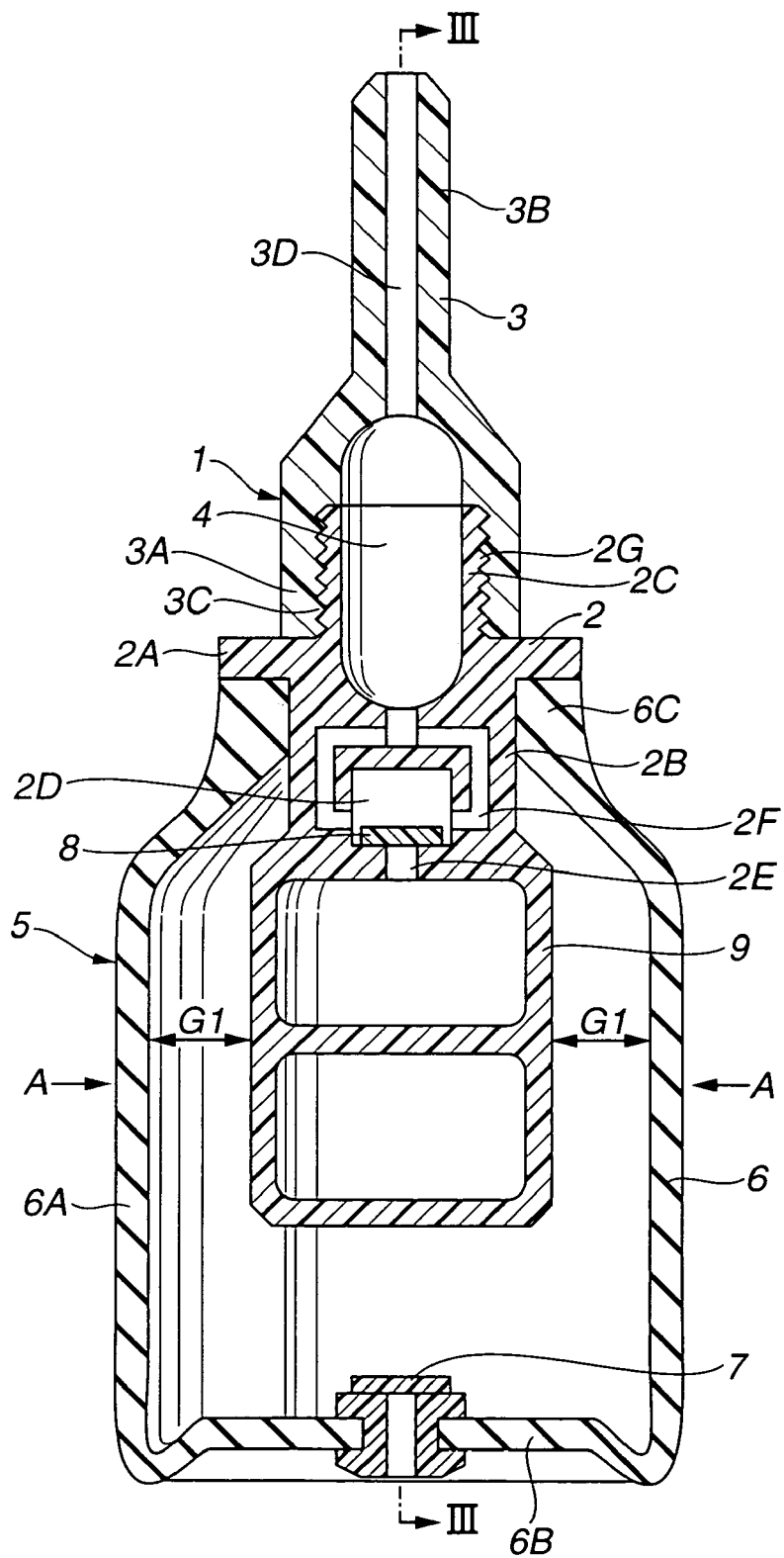
FIG. 2 is a vertical cross-sectional view of the medicine administering device of FIG. 1.
Figure 3:
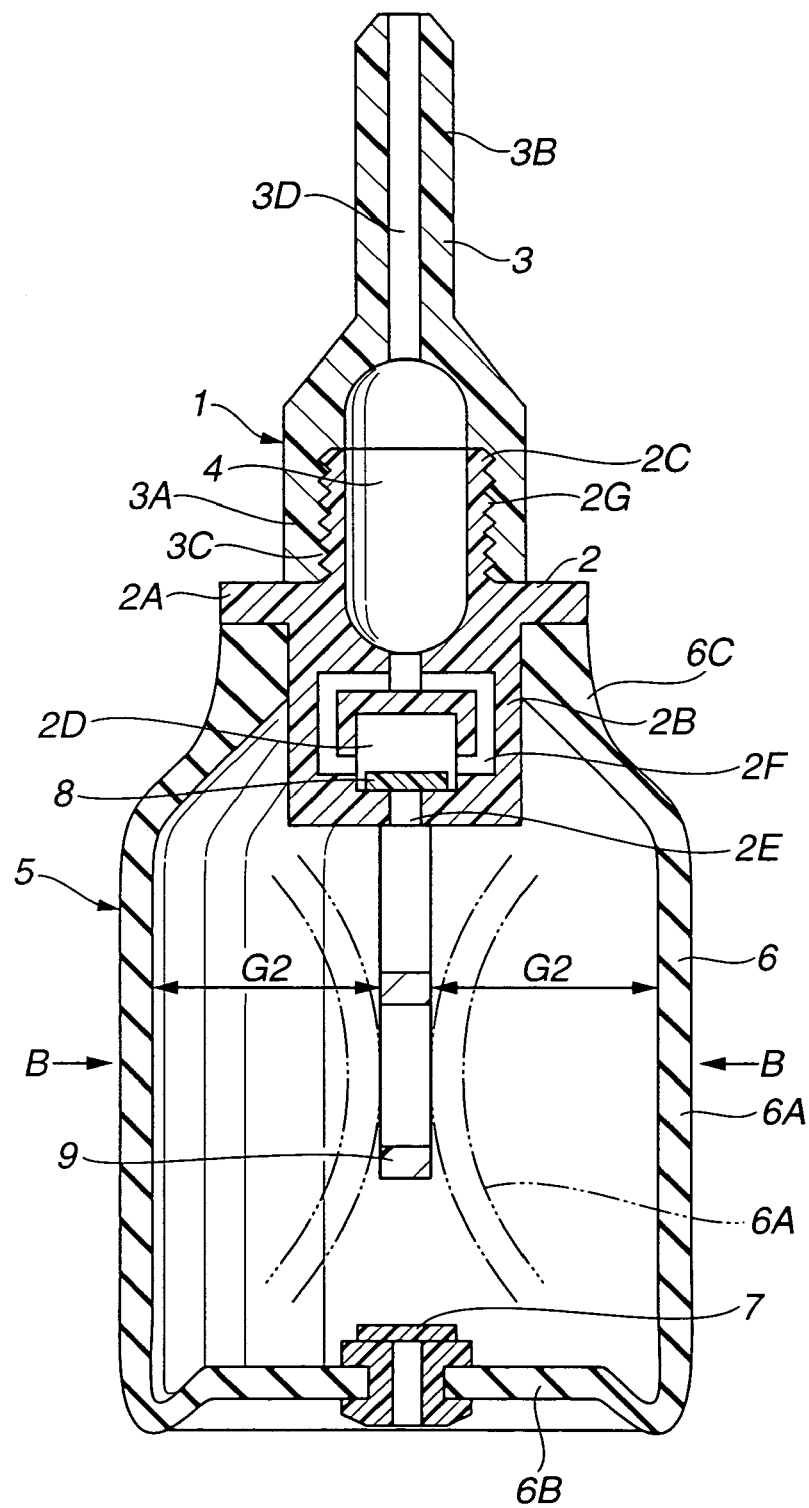
FIG. 3 is a vertical cross-sectional view taken in the direction of arrows substantially along the line of III-III of FIG. 2.
Figure 4:
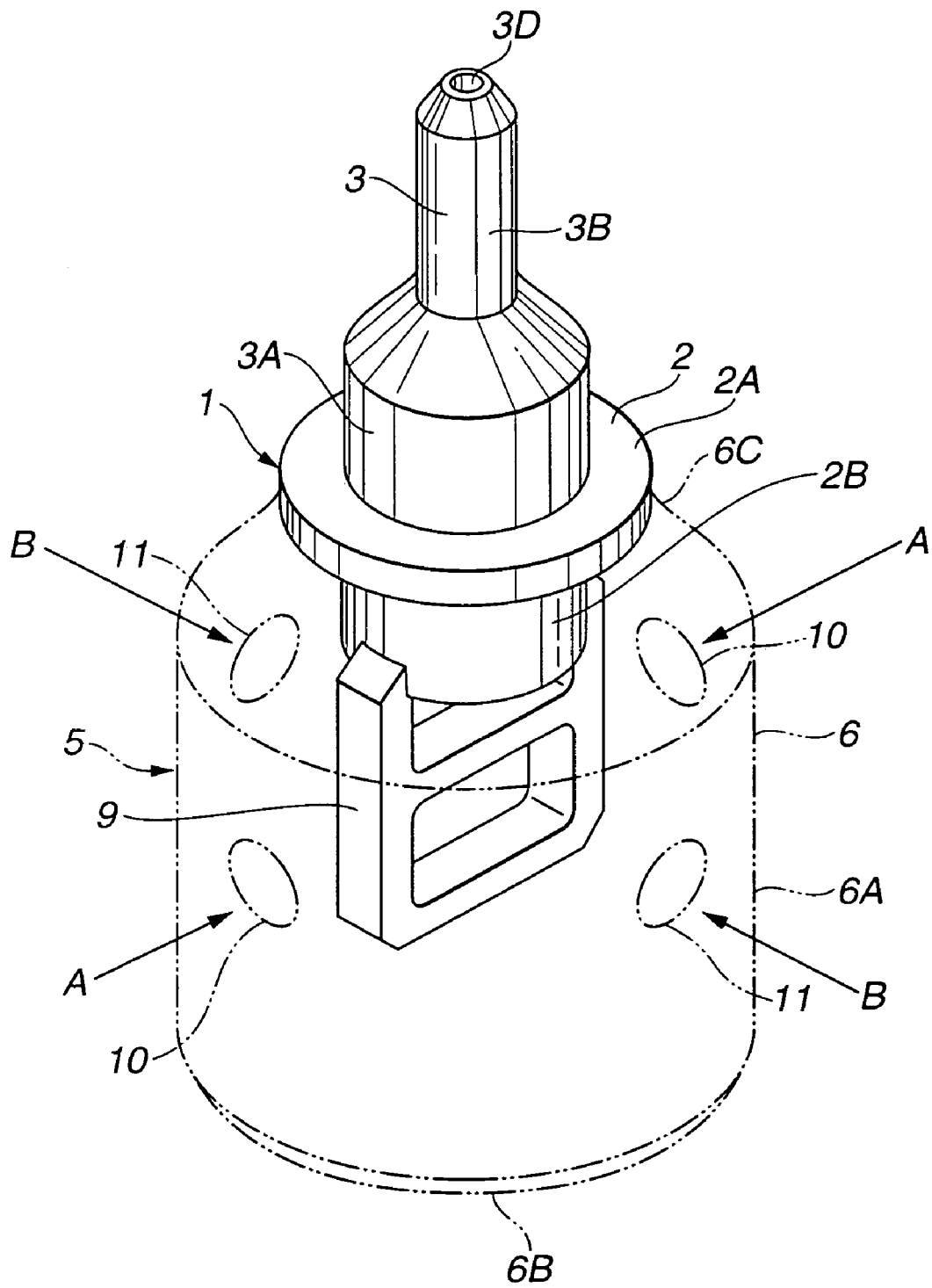
FIG. 4 is a perspective view of a medicine administering device main body of the medicine administering device of FIG. 1, indicating a movable diaphragm body of a pump in phantom.

As shown in FIG. 4, restriction member 9 is formed as a plate member and integral with passage-forming section 2B of holder 2 and extends vertically downwardly. Restriction member 9 as the plate member has a frame-like structure and takes a generally inversed A-shape so that two large through-openings (no numerals) are formed. Accordingly, as shown in FIG. 2, restriction member 9 provides two smaller distances (dimensions) G1 each of which is between the inner surface of cylindrical section 6A of movable diaphragm body 6 and the side edge of restriction member 9, or in a direction of width of restriction member 9 (i.e., a first pressing direction A). Besides, as shown in FIG. 3, restriction member 9 provides two larger distances (dimensions) G2 each of which is between the inner surface of cylindrical section 6A of movable diaphragm body 6 and the flat surface of restriction member 9, or in a direction of thickness of restriction member 9 (i.e., a second pressing direction B).

Restriction member 9 allows movable diaphragm body 6 to collapse by the smaller distance G1 as shown in FIGS. 2 and 5 when movable diaphragm body 6 is pressed in the first pressing directions A, A, thereby restricting the inward movement of movable diaphragm body 6 so that movable diaphragm body 6 takes the smaller inward displacement amount. In contrast, restriction member 9 allows movable diaphragm body 6 to collapse by the larger distance G2 as indicated in phantom in FIG. 3 when movable diaphragm body 6 is pressed in the second pressing directions B, B, thereby relaxing the restriction in the inward movement of movable diaphragm body 6 so that movable diaphragm body 6 can take the larger inward displacement amount.

The pressing of movable diaphragm body 6 in the first pressing directions can be accomplished by two pressing marks 10, 10 which are provided respectively at the symmetrical positions relative to a first imaginary plane passing through the axis of main body 1, and are at the outer peripheral surface of cylindrical section 6A of movable diaphragm body 6 as shown in FIGS. 1 and 4. In contrast, the pressing of movable diaphragm body 6 in the second pressing directions can be accomplished by two pressing marks 11, 11 which are provided respectively at the symmetrical positions relative to a second imaginary plane (perpendicular to the first imaginary plane) passing through the axis of main body 1, and are at the outer peripheral surface of cylindrical section 6A of movable diaphragm body 6 as shown in FIGS. 1 and 4. In this connection, the plate member as restriction member 9 is located parallel with the above-mentioned first imaginary plane as seen in FIG. 4.

The medicine administering device according to the first embodiment is constructed and arranged as discussed above and is operated in use as follows:

First, a preparation operation for medicine administration will be discussed. In this preparation operation, spray nozzle 3 is detached from holder 2, and then the capsule K filled with powdery medicine is accommodated within the powdery medicine accommodating chamber 4. Then, after spray nozzle 3 is installed to holder 2, a hole is formed in the capsule K by using a hole-forming needle (not shown).

Subsequently, an administration operation for the powdery medicine will be discussed. At an initial medicine administration operation, movable diaphragm body 6 is put between the fingers of the patient in such a manner as to press the positions of first pressing marks 10, 10 with the fingertips, and then the tip of nozzle section 3B of spray nozzle 3 is inserted, for example, into the left nasal cavity of the left and right nasal cavities.

Thereafter, as shown in FIG. 5, cylindrical section 6A of movable diaphragm body 6 is pressed in the first pressing directions A, A with the fingertips in such a manner as to collapse cylindrical section 6A. At this time, the wall of cylindrical section 6A of movable diaphragm body 6 is brought into contact with the side edges of the restriction member 9 upon being inwardly moved by the smaller distance G1, so that the inward displacement amount of movable diaphragm body 6 becomes small thereby making small the amount of air discharged by pump 5. By this, air stream discharged from pump 5 opens discharge valve 8 and flows into the capsule K accommodated within powdery medicine accommodating chamber 4, and then sprayed together with the powdery medicine in the capsule K from nozzle section 3B of spray nozzle 3 into the left nasal cavity. The amount of the sprayed powdery medicine at this time can be suppressed to about half of the whole amount of the powdery medicine filled in the capsule K by reducing the amount of air discharged from pump 5.

Next, after completion of the administration operation to the left nasal cavity, a subsequent administration operation to the right nasal cavity will be made. In this administration operation, positions at which movable diaphragm body 6 is put between the fingers are changed from the first pressing marks 10, 10 to the second pressing marks 11, 11 which are located at the positions which lie in the direction perpendicular to the direction in which first pressing marks 11, 11 lie. Then, the tip end of spray nozzle 3 is inserted into the right nasal cavity.

Thereafter, as shown in phantom in FIG. 3, cylindrical section 6A of movable diaphragm body 6 is pressed in the second pressing directions B, B with the fingertips in such a manner as to collapse movable diaphragm body 6. At this time, the wall of cylindrical section 6A of movable diaphragm body 6 is brought into contact with the flat surface of the restriction member 9 upon being inwardly moved by the larger distance G2, so that the inward displacement amount of movable diaphragm body 6 becomes large thereby making large the amount of air discharged by pump 5. By this, a large amount of air is flown from pump 5, thereby spraying into the right nasal cavity the whole amount (i.e., about half of the powdery medicine originally filled in the capsule K) of the powdery medicine remaining in the capsule K.

Thus, according to the first embodiment medicine administering device, pump 5 is provided therein with restricting member 9 which is arranged to restrict the displacement amount of movable diaphragm body 6 to be smaller when movable diaphragm body 6 is pressed in the first pressing directions A, A, and to restrict the displacement amount of movable diaphragm body 6 to be larger when movable diaphragm body 6 is pressed in the second pressing directions B, B.

Hence, when the powdery medicine is first administered into one of the left and right nasal cavities, the cylindrical section 6A of movable diaphragm body 6 is pressed in the first pressing directions so as to make small the inward displacement amount of movable diaphragm body 6, thereby limiting the sprayed amount of the powdery medicine to about half of the whole amount of the powdery medicine originally filled in the capsule K. When the powdery medicine is administered into the other nasal cavity, cylindrical section 6A of movable diaphragm body 6 is pressed in the second pressing directions B, B so as to make large the inward displacement amount of movable diaphragm body 6 upon relaxing the restriction of the restriction member 9, thereby spraying the whole amount of the powdery medicine remaining in the capsule K.

As a result, the powdery medicine can be equally administered into the left and right nasal cavities by such a simple operation as to select the pressing positions of movable diaphragm body 6 of pump 5. Additionally, the powdery medicine administration operation can be completed with one administration operation to one of the left and right nasal cavities and one administration operation to the other nasal cavity, thus facilitating the administration operation for the powdery medicine to the patient. Further, since movable diaphragm body 6 of pump 5 is provided at its outer peripheral surface with the first pressing marks 10, 10 and the second pressing marks 11, 11, the patient can confirm the pressing marks 10, 11 with his or her naked eye and complete the powdery medicine administration operation by pressing movable diaphragm body 6 in accordance with the orders of the pressing marks 10, 11. Furthermore, restriction member 9 is formed of the plate member, and therefore the arrangement of the medicine administering device can be simplified while lowering a production cost of the medicine administering device. Besides, restriction member 9 can be readily provided to an existing medicine administering device for nasal cavities.

According to the above embodiment, the plate member serving as the restricting device is fixedly disposed within the bottle-shaped movable diaphragm body of the pump and extends axially in the pump. The displacement amount of the bottle-shaped movable diaphragm body is relatively small when the bottle-shaped movable diaphragm body is pressed in the direction of width of the plate member whereas the displacement amount of the bottle-shaped movable diaphragm body is relatively large when the bottle-shaped movable diaphragm body is pressed in the direction of thickness of the plate member. With such an arrangement, the displacement amount of the pump can be easily changed under the inherent shape of the plate member, by virtue of merely providing the plate member in the pump.

Figure 6:
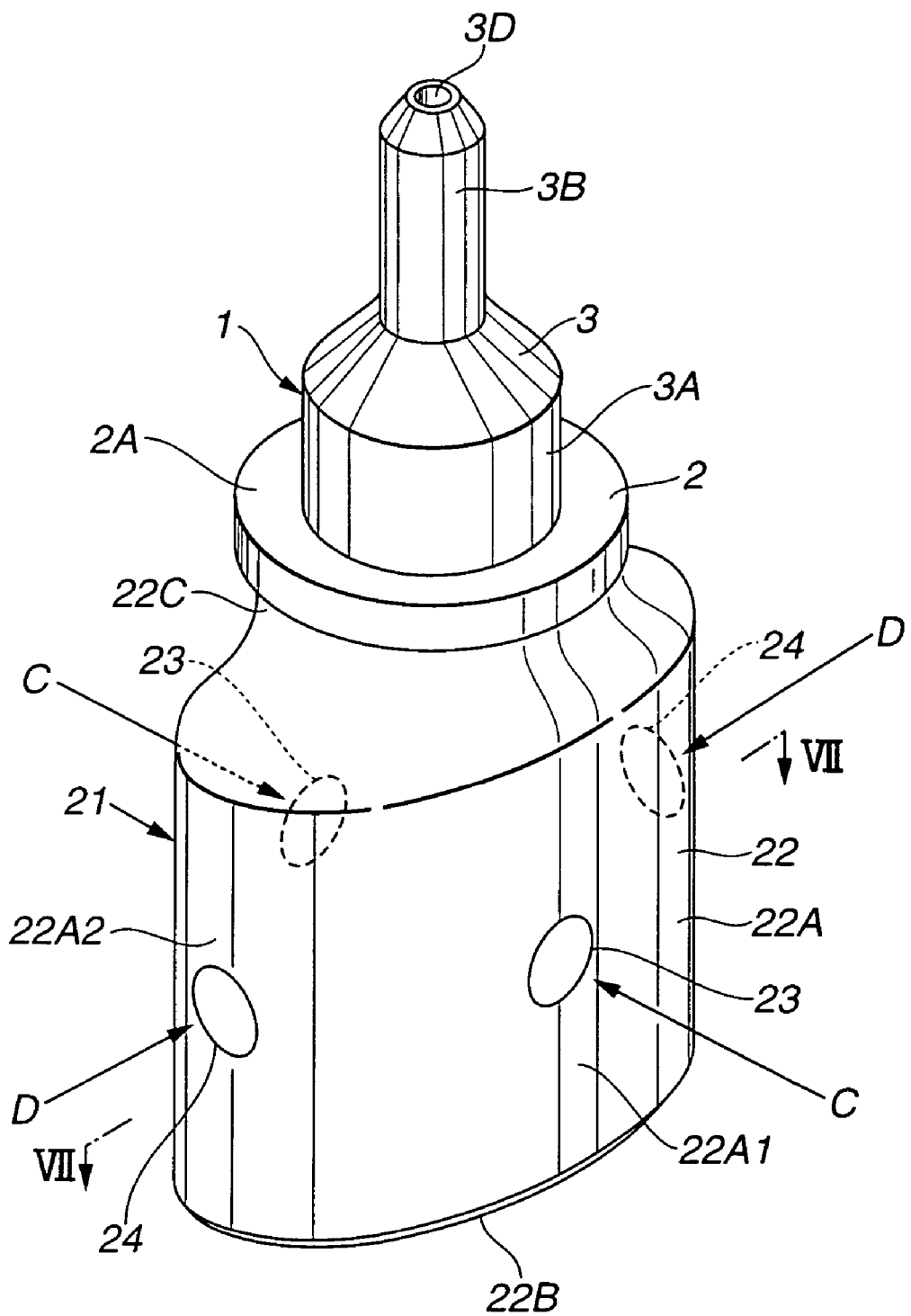
FIG. 6 is a perspective view of a second embodiment of the medicine administering device according to the present invention.
Figure 7:
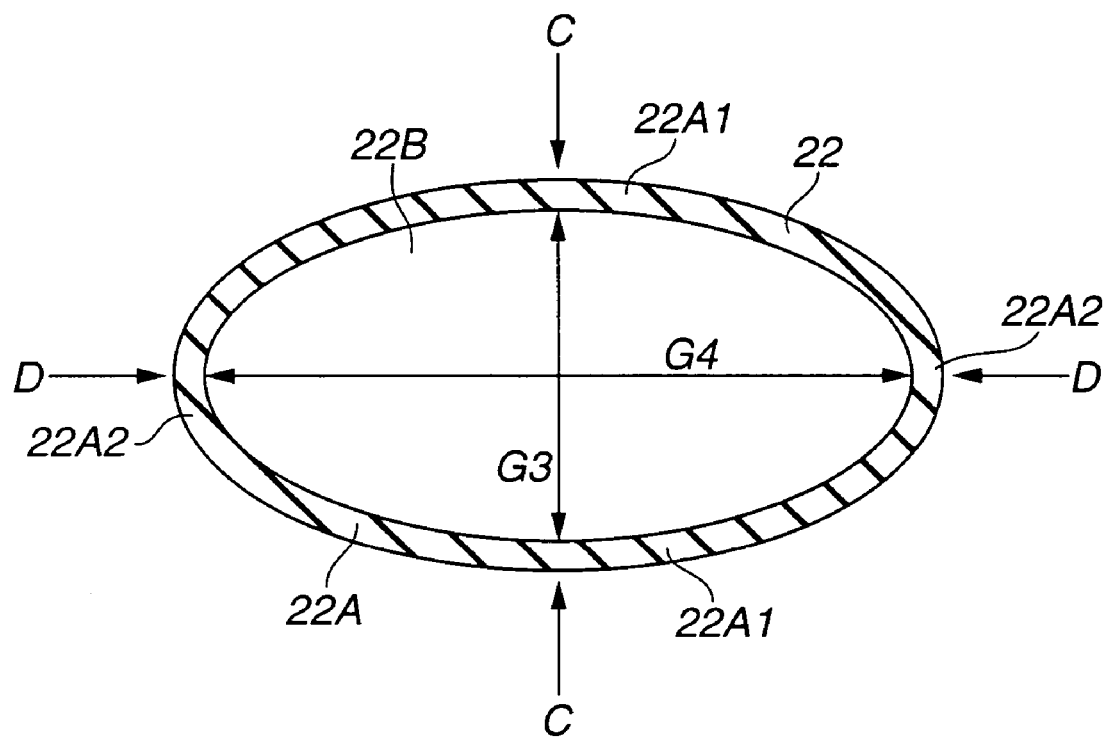
FIG. 7 is a transverse cross-sectional view of a movable diaphragm body of a pump of the medicine administering device of FIG. 6, taken in the direction of arrows substantially along the line of VII-VII of FIG. 6.

FIGS. 6 and 7 illustrates a second embodiment of the medicine administering device for nasal cavities, according to the present invention. The second embodiment medicine administering device is similar to the first embodiment medicine administering device shown in FIGS. 1 to 5 with the exception that the pump is constituted of a flat cylindrical movable diaphragm body having a generally elliptical transverse cross-section (or elongate loop-shaped transverse cross-section), omitting the restriction member within the movable diaphragm body in the first embodiment.

In this embodiment, pump 21 is used in place of pump 5 in the first embodiment medicine administering device. Pump 21 is generally constituted of movable diaphragm body 22 (discussed after), and suction and discharge valves 7, 8 which are the same in the first embodiment medicine administering device. As shown, movable diaphragm body 22 a flat cylindrical body having an elongate loop-shaped transverse cross-section to restrict a displacement amount of the pump in accordance with first and second kinds of pressing positions at which the pump is pressed, Movable diaphragm body 22 constitutes an outer part of pump 21 and is formed of a rubber (elastomeric) material having an elasticity. More specifically, movable diaphragm body 22 includes a relatively large diameter cylindrical section 22A. Cylindrical section 22A of movable diaphragm body 22 has an elongate (or elliptical) loop-shaped transverse cross-section which is on an imaginary plane perpendicular to the axis of medicine administering device main body 1. An elliptical and disc-shaped bottom section 22B is integral with cylindrical section 22A and located to close the bottom of cylindrical section 22A. An installation mouth section 22C is integral with cylindrical section 22A and formed at an open upper end side of cylindrical section 22A. Installation mouth section 22C of movable diaphragm body 22 is fitted to the outer peripheral side of holder 2 in such a manner to maintain an air-tight seal between installation mouth section 22C and holder 2. Additionally, cylindrical section 22A of movable diaphragm body 22 is provided at its outer surface with pressing marks 23, 24 which will be discussed after.

Here, as shown in FIGS. 6 and 7, cylindrical section 22A of movable diaphragm body 22 is formed having a generally elliptical transverse cross-section which is perpendicular to the axis of the medicine administering device main body 1. Cylindrical section 22A has a pair of gently curved wall sections 22A1, 22A1 which are spaced from each other with a smaller distance (dimension) G3 and opposite to each other, and a pair of sharply curved wall sections 22A2, 22A2 which are spaced from each other with a larger distance (dimension) G4 and opposite to each other. Gently curved wall sections 22A1, 22A1 lie in first pressing directions C, C while sharply curved wall sections 22A2, 22A2 lie in second pressing directions D, D which are perpendicular to the first pressing directions C, C.

With the above arrangement, when gently curved wall sections 22A1, 22A1 are pressed in the first pressing directions C, the gently curved wall sections 22A1, 22A1 are brought into contact with each other upon being inwardly displaced by the smaller distance G3, thereby restricting the inward displacement amount of gently curved wall sections 22A1, 22A1. By this, the amount of air discharged from pump 21 becomes small, thus spraying about half of the whole powdery medicine filled in the capsule K. In contrast, when sharply curved wall sections 22A2, 22A2 are pressed in the second pressing directions, sharply curved wall sections 22A2, 22A2 can be largely inwardly displaced under the effect of the larger distances G4. By this, the amount of air discharged from pump 21 becomes large, thereby spraying the whole amount (i.e., about half of the powdery medicine originally filled in the capsule K) of the powdery medicine remaining in the capsule K.

First pressing marks 23, 23 are provided at the surfaces of gently curved wall sections 22A1, 22A1 of cylindrical section 22A of movable diaphragm body 22. First pressing is made at first pressing marks 23, 23 in the first pressing directions C, C in order to accomplish an initial medicine administration operation for administering the powdery medicine into one of the left and right nasal cavities of the patient. Second pressing marks 24, 24 are provided at the surfaces of sharply curved wall sections 22A2, 22A2 of cylindrical section 22A of movable diaphragm body 22. Subsequent pressing is made at the second pressing marks 24, 24 in the second pressing directions D, D in order to accomplish a subsequent medicine administration operation for administering the powdery medicine into the other nasal cavity.

Thus, also in the second embodiment medicine administering device, generally the same effects as those in the first embodiment medicine administering device can be obtained. Particularly in the second embodiment medicine administering device, the arrangement can be simplified while reducing the production cost.

While the movable diaphragm body has been shown and described as being cylindrical and having the generally elliptical transverse cross-section in the second embodiment medicine administering device, it will be appreciated that the movable diaphragm body is not limited to one having such a structure, so that the movable diaphragm body may be formed to be flatly cylindrical, for example, to be cylindrical and have an elongate or stretched elliptical transverse cross-section or to be cylindrical and have an elongate or stretched rectangular transverse cross-section.

Although the capsule K filled with the powdery medicine has been shown and described as being accommodated within medicine accommodating chamber 4 in the first and second embodiments, it will be understood that an arrangement for accommodating the powdery medicine may not be limited to this, in which the powdery medicine may be, for example, directly filled within medicine accommodating chamber 4.

The entire contents of Japanese Patent Application No. 2003-058837, filed Mar. 5, 2003, is incorporated herein by reference.

What is claimed is:

1. A medicine administering device for nasal cavities, comprising:
    a medicine administering device main body including a part defining a powdery medicine accommodating chamber, and a spray nozzle located at a tip end side of the main body;
    a pump disposed at a base end side of the medicine administering device main body to discharge air within the pump through the powdery medicine accommodating chamber to the spray nozzle upon being pressed from an outside of the pump, said tip end and said base end defining opposed axial positions of said main body; and
    a restricting device, having first opposed surfaces and a first transverse width and second opposed surfaces perpendicular to said first opposed surfaces and a second transverse width, where said first width is greater than said second width, disposed within the pump and operative to restrict a displacement amount of the pump in accordance with first and second kinds of pressing positions at which the pump is pressed, the first and second kinds of pressing positions lying respectively in first and second directions, which are perpendicular to each other and respectively at first and second axial positions including the same axial position,
    whereby a constant amount of medicine can be administered by pressing at plural axial positions between said tip end and said base end.

2. A medicine administering device as claimed in claim 1, wherein the pump includes a bottle-shaped movable diaphragm body.

3. A medicine administering device as claimed in claim 2, wherein the bottle-shaped movable diaphragm body has an open end section which is sealingly fitted to a part of the medicine administering device main body.

4. A medicine administering device as claimed in claim 2, wherein the pump includes a one-way suction valve through which air is able to be sucked into the bottle-shaped movable diaphragm body, the suction valve being installed to a wall of the bottle-shaped movable diaphragm body.

5. A medicine administering device as claimed in claim 4, wherein the pump includes a one-way discharge valve through which air is able to be discharged from the bottle-shaped movable diaphragm body and supplied to the powdery medicine accommodating chamber, the discharge valve being installed to a part of the medicine administering device main body.

6. A medicine administering device as claimed in claim 2, wherein the bottle-shaped movable diaphragm body is provided at its surface with first and second kinds of marks which respectively indicate the first and second kinds of pressing positions.

7. A medicine administering device as claimed in claim 1, wherein the restricting device restricts a displacement amount of a wall of the pump.

* * * * *